United States Patent
Uchiyama

(10) Patent No.: US 7,850,006 B2
(45) Date of Patent: Dec. 14, 2010

(54) MEDICAL APPARATUS CONTAINING DEVICE, DISCARDING DEVICE AND METHOD OF USE OF MEDICAL APPARATUS

(75) Inventor: Akio Uchiyama, Yokohama (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 12/145,587

(22) Filed: Jun. 25, 2008

(65) Prior Publication Data

US 2008/0257768 A1 Oct. 23, 2008

Related U.S. Application Data

(63) Continuation of application No. PCT/JP2006/326140, filed on Dec. 27, 2006.

(30) Foreign Application Priority Data

Dec. 27, 2005 (JP) ............................. 2005-375531

(51) Int. Cl.
*A61B 19/02* (2006.01)
*A61B 1/04* (2006.01)

(52) U.S. Cl. ...................... 206/438; 206/350; 206/363; 206/818; 348/77; 600/121

(58) Field of Classification Search ................ 206/350, 206/363–370, 438; 348/68, 76–77; 600/109–114, 600/121

See application file for complete search history.

(56) References Cited

U.S. PATENT DOCUMENTS 7,295,226 B1 * 11/2007 Meron et al. ................. 348/77

7,511,733 B2 * 3/2009 Takizawa et al. .............. 348/77
7,553,274 B2 * 6/2009 Miyake et al. ............... 600/121

FOREIGN PATENT DOCUMENTS

| JP | 2003-523795 | 8/2003 |
|---|---|---|
| JP | 2004-255174 | 9/2004 |
| JP | 2005-095433 | 4/2005 |
| JP | 2005-103091 | 4/2005 |
| JP | 2005-124962 | 5/2005 |
| JP | 2005-192631 | 7/2005 |
| WO | WO 01/35813 | 5/2001 |
| WO | WO 2005/072068 | 8/2005 |

OTHER PUBLICATIONS

International Search Report, dated Mar. 13, 2007, issued in corresponding PCT Application No. PCT/JP2006/326140.
Office Action issued by the Chinese Patent Office on Jan. 22, 2010 in connection with corresponding Chinese Patent Application No. 2006800493498.
Translation of Office Action issued by the Chinese Patent Office on Jan. 22, 2010 in connection with corresponding Chinese Patent Application No. 2006800493498.

* cited by examiner

*Primary Examiner*—Bryon P Gehman
(74) *Attorney, Agent, or Firm*—Ostrolenk Faber LLP

(57) ABSTRACT

A container case contains a capsule endoscope which incorporates a magnet. A magnetic body is disposed so as to guide, from one magnetic pole to the other magnetic pole, a magnetic field which is generated from the magnet of the capsule endoscope that is accommodated between and positioned by a first hold portion of an outer case and a second hold portion of an inner case which position the capsule endoscope. Thereby, there is provided a capsule medical apparatus containing device which can facilitate handling of a capsule medical apparatus and can enhance the efficiency in storage of the capsule medical apparatus.

7 Claims, 9 Drawing Sheets

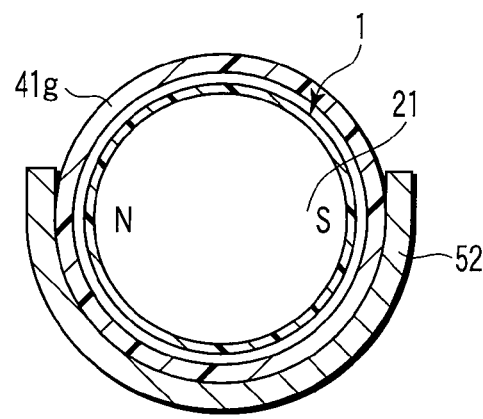
F I G. 11
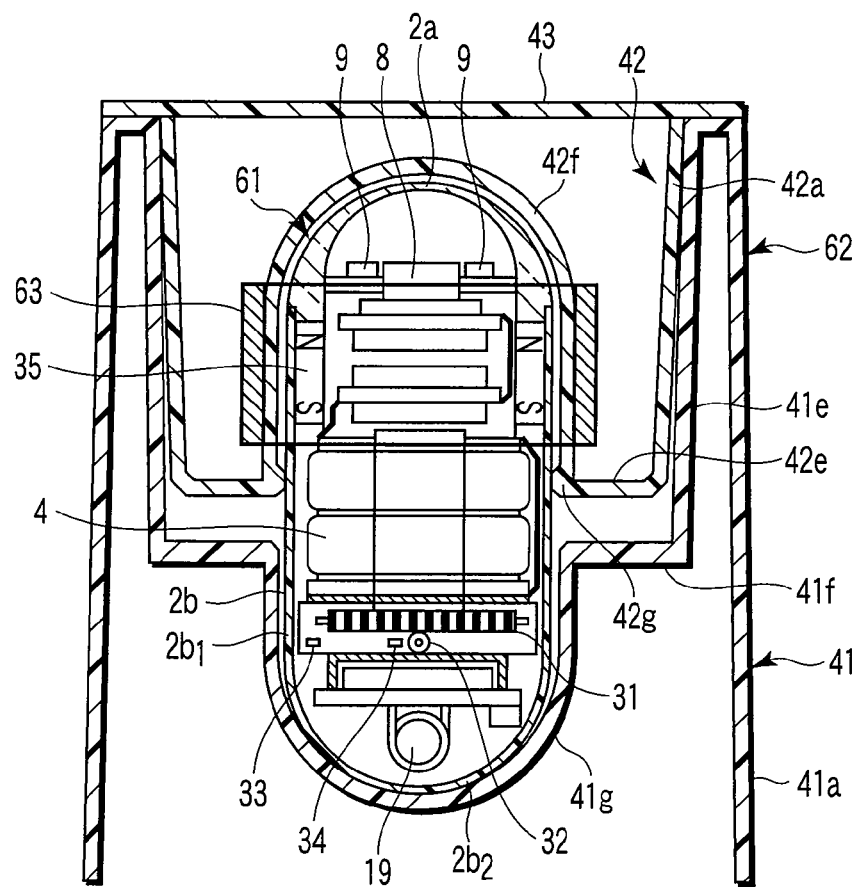
F I G. 12

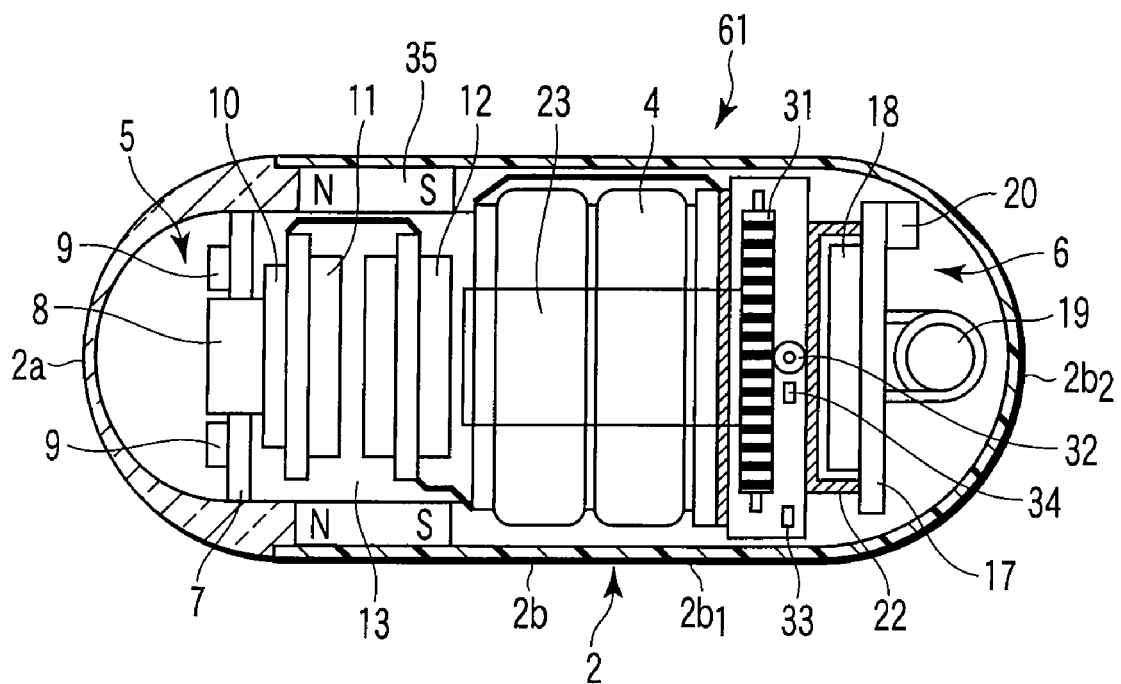
F I G. 13
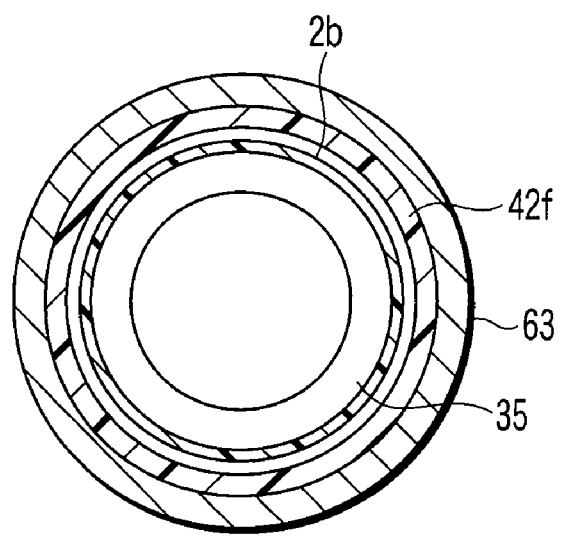
F I G. 14

MEDICAL APPARATUS CONTAINING DEVICE, DISCARDING DEVICE AND METHOD OF USE OF MEDICAL APPARATUS

CROSS REFERENCE TO RELATED APPLICATIONS

This is a Continuation Application of PCT Application No. PCT/JP2006/326140, filed Dec. 27, 2006, which was published under PCT Article 21(2) in Japanese.

This application is based upon and claims the benefit of priority from prior Japanese Patent Application No. 2005-375531, filed Dec. 27, 2005, the entire contents of which are incorporated herein by reference.

BACKGROUND OF THE INVENTION

1. Field of the Invention

The present invention relates to a medical apparatus containing device which contains a medical apparatus that incorporates a magnet, to a discarding device, and to a method of use of a medical apparatus. In particular, the invention relates to a capsule medical apparatus containing device which contains a capsule medical apparatus that incorporates a magnet.

2. Description of the Related Art

A capsule-type endoscope is generally known, which is ingested by a subject who is an examined body and which observes (examines) the inside of a tubular organ in the body, for instance, the inside (body cavity) of the organ such as the esophagus, stomach or small intestine. Jpn. Pat. Appln. KOKAI Publication No. 2004-255174 (patent document 1) discloses a capsule-type endoscope of a magnetic guidance type in which a capsule-type endoscope is guided in a desired direction to a desired position in the body by a magnetic guidance system which generates a magnetic field.

The pamphlet of International Publication 01/35813 (patent document 2) discloses a structure wherein a package for controlling the driving of a capsule endoscope is provided, and the capsule endoscope is contained in this package. A reed switch, which is turned on/off by an external magnetic field, is included in the capsule endoscope. A permanent magnet, which supplies the external magnetic field, is included in the package. Specifically, the reed switch, which is included in the capsule endoscope, is configured to be kept in the OFF state in an environment in which a magnetic field of a predetermined strength or more is applied, and to be turned on when the intensity of the external magnetic field lowers. Thus, in the state in which the capsule endoscope is contained in the package, the capsule endoscope is not driven. When the capsule endoscope is to be ingested, the capsule endoscope is taken out of the package. Thereby, the capsule endoscope is isolated from the permanent magnet and becomes free from the influence of the magnetic force. Thus, the driving of the capsule endoscope is started. With this structure, in the state in which the capsule endoscope is contained in the package, the driving of the capsule endoscope is prevented. After the capsule endoscope is taken out of the package, capture of an image by an image pickup function of the capsule endoscope and transmission of an image signal by a wireless function are performed.

BRIEF SUMMARY OF THE INVENTION

According to a first aspect of the present invention, a medical apparatus containing device which contains a medical apparatus which incorporates a magnet, comprising: positioning means for positioning the medical apparatus; and a magnetic body which is so disposed as to guide a magnetic field, which is generated from the magnet of the medical apparatus that is positioned by the positioning means, from one magnetic pole to the other magnetic pole.

In the above-described structure, when the capsule medical apparatus is set in the containing device which contains the medical apparatus which incorporates the magnet, the capsule medical apparatus is positioned in a predetermined set position by the positioning means. In this state, the magnetic field, which is generated from the magnet of the capsule medical apparatus, is guided from one magnetic pole of the magnet of the capsule medical apparatus to the other magnetic pole via the magnetic body of the containing device.

Preferably, the magnetic body is formed as a thin film.

Preferably, the thin film is coated with a resin material.

Preferably, an adhesive member is attached to the resin material, and the resin material is attached to at least one of the medical apparatus and the medical apparatus containing device.

Preferably, the magnetic body is positioned to at least one of the medical apparatus and the medical apparatus containing device by an attractive force acting between the magnetic body and the magnet.

Preferably, the medical apparatus is a capsule medical apparatus.

Preferably, the capsule medical apparatus is a capsule endoscope.

According to second aspect of the present invention, a medical apparatus containing device comprising: a container case which contains a medical apparatus which incorporates a magnet; positioning means for positioning the medical apparatus in the container case; and magnetic force reduction preventing means for preventing reduction in magnetic force of the magnet, the magnetic force reduction preventing means being disposed at a position that is away from the magnet and corresponds to the magnet of the medical apparatus which is positioned and contained in the container case.

Preferably, the magnetic force reduction preventing means includes a magnetic body which is disposed at a position that corresponds to the magnet of the medical apparatus, which is positioned and contained in the container case, in a state in which the magnetic body surrounds the magnet, and the magnetic body is so disposed as to guide a magnetic field, which is generated from the magnet, from one magnetic pole to the other magnetic pole.

Preferably, the magnetic body is composed of a U-shaped member which is formed in a U shape, the U-shaped member is disposed on the container case in a vicinity of the respective magnetic poles of the magnet, and the magnetic force reduction preventing means forms a magnetic circuit between the U-shaped member and the magnet, thereby decreasing a magnetic field which leaks from the magnet to an outside of the container case, and preventing reduction in magnetic force of the magnet.

Preferably, the medical apparatus is a capsule medical apparatus, the container case includes an outer case having a first hold portion with a recess shape, which holds a part of the capsule medical apparatus, and an inner case having a second hold portion with a recess shape, which holds another part of the capsule medical apparatus, and the magnetic body is mounted on an outside of at least one of the first hold portion of the outer case and the second hold portion of the inner case.

Preferably, the magnetic body is formed as a thin film.

Preferably, the thin film is coated with a resin material.

Preferably, an adhesive member is attached to the resin material, and the resin material is attached to at least one of the medical apparatus and the medical apparatus containing device.

Preferably, the magnetic body is positioned to at least one of the medical apparatus and the medical apparatus containing device by an attractive force acting between the magnetic body and the magnet.

Preferably, the medical apparatus is a capsule medical apparatus.

According to third aspect of the present invention, a method of use of a medical apparatus, comprising: a step of keeping a magnetic body, which guides magnetic force lines from one magnetic pole to the other magnetic pole of a magnet which is provided in the medical apparatus, in a vicinity of the medical apparatus; a step of increasing a distance between the magnetic body and the magnet; and a step of inserting the medical apparatus into a body cavity.

According to forth aspect of the present invention, a method of use of a medical apparatus, comprising: a step of keeping a magnetic body, which forms a magnetic circuit for guiding magnetic force lines from one magnetic pole to the other magnetic pole of a magnet which is provided in the medical apparatus, in a vicinity of the medical apparatus; a step of cutting off the magnetic circuit; and a step of inserting the medical apparatus into a body cavity.

BRIEF DESCRIPTION OF THE SEVERAL VIEWS OF THE DRAWING

FIG. 11 is a transverse cross-sectional view showing a modification of the magnetic body which is attached to the container case of the capsule endoscope according to the second embodiment;

FIG. 12 is a longitudinal cross-sectional view showing the state in which a capsule endoscope is contained in a container case of the capsule endoscope according to a third embodiment of the present invention;

FIG. 13 is a longitudinal cross-sectional view showing the capsule endoscope according to the third embodiment;

FIG. 14 is a transverse cross-sectional view showing the state of attachment of a magnetic body which is attached to the container case of the capsule endoscope according to the third embodiment;

DETAILED DESCRIPTION OF THE INVENTION

Figure 1:
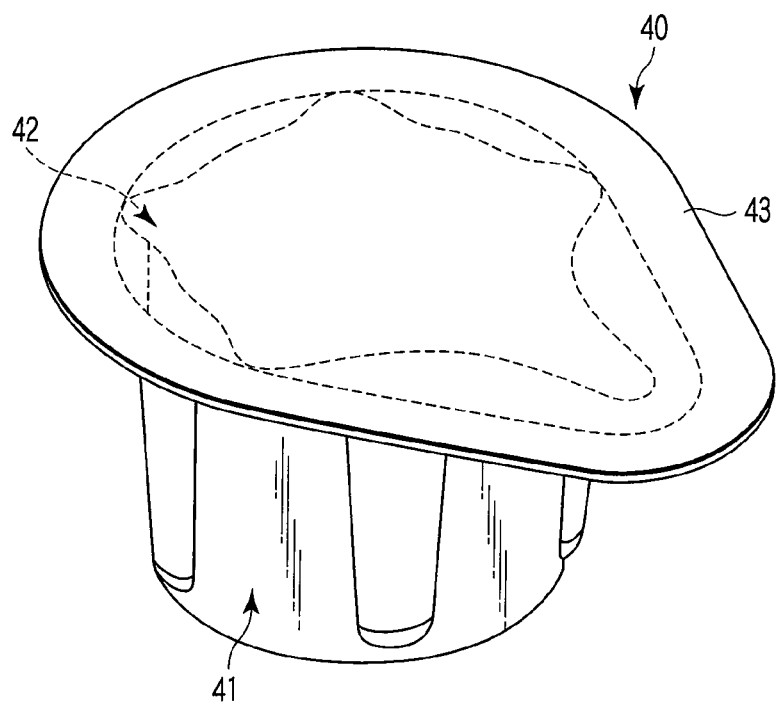
FIG. 1 is a perspective view showing the structure of a container case of a capsule endoscope according to a first embodiment of the present invention.

A first embodiment of the present invention will now be described with reference to FIG. 1 to FIG. 8. FIG. 1 shows a container case (containing device) 40 of a capsule medical apparatus according to the present embodiment. The container case 40 contains an ingestion-type capsule endoscope 1 (see FIG. 8) which is a magnetic guidance type capsule medical apparatus that includes a magnet.

Figure 8:
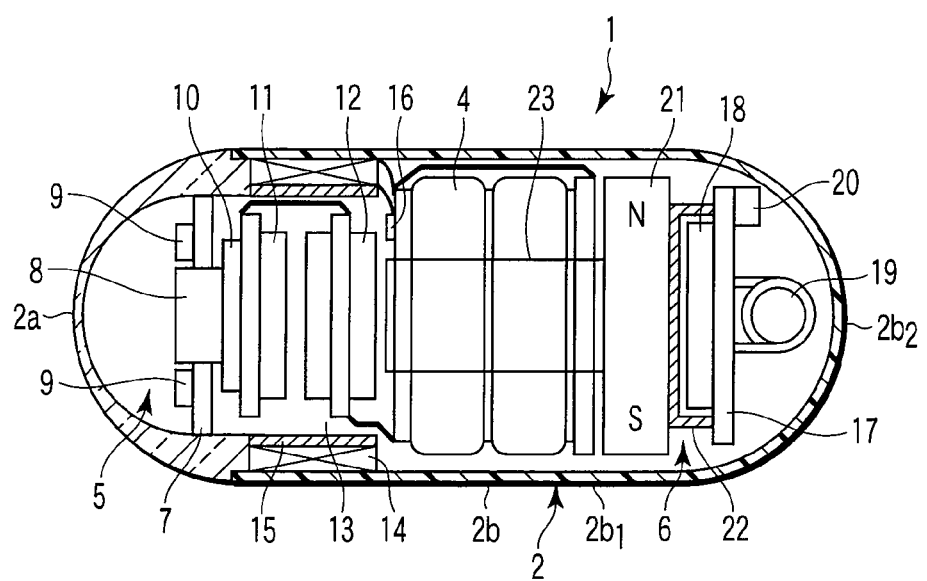
FIG. 8 is a longitudinal cross-sectional view showing the capsule endoscope according to the first embodiment.

The capsule endoscope 1 is configured as shown in FIG. 8. Specifically, the capsule endoscope 1 includes a sealed container 2 which is an armor case. The sealed container 2 has such a size as to permit ingestion by a human, and includes a substantially hemispherical front end cover 2a and a cylindrical body cover 2b. The front end cover 2a and the body cover 2b are elastically engaged, and the inside is liquid-tightly sealed, and thus the armor case is formed.

The front end cover 2a has a substantially hemispherical dome shape, and a rear side of the dome is opened in a circular shape. The distal end cover 2a is formed of a transparent material having transparency or light transmissivity, for example, a synthetic resin material, such as cycloolefin polymer or polycarbonate, which is preferable in ensuring optical performance and strength.

The body cover 2b is positioned at the rear end of the front end cover 2a and is a member for covering structural elements of the capsule endoscope 1 such as illumination means, image pickup means, a battery and wireless transmission means, which will be described later. The body cover 2b is configured such that a circular cylindrical body portion 2b1 and a substantially hemispherical dome-shaped rear end portion 2b2 are integrally formed, and a front side of the body portion 2b1 is opened in a circular shape. The body cover 2b is formed of an opaque synthetic resin material, such as polysulfone, which is preferable in ensuring strength. In the inside of the sealed container 2, a battery 4 is disposed at a substantially central position between the front end cover 2a and the dome-shaped rear end portion 2b2. An observation unit 5 is disposed on the front end cover 2a side of the battery 4, and a communication unit 6 is disposed on the dome-shaped rear end portion 2b2 side of the battery 4.

In the observation unit 5, a support member 7 is disposed at a position spaced apart from and opposed to an inner peripheral surface of the front end cover 2a. A lens 8 of an observation optical system is disposed at a substantially central position of the support member 7, and a plurality of light-emitting elements 9 such as LEDs, which emit illumination light for illuminating, for instance, an examined body part in a body cavity, are disposed around the lens 8. A solid image pickup element 10 such as a CCD or a CMOS (hereinafter represented by CCD 10), which receives reflective light of the illumination light and captures an image of the examined body part, is disposed behind the lens 8. An image processing circuit 11 and a power supply circuit 12 are disposed behind the CCD 10.

Further, a coil (magnetic induction coil) 14, which has a maximum outside dimension that is slightly less than the inside diameter of the sealed container 2, is disposed on an outer peripheral surface of a mold member 13 in which the image processing circuit 11 and a power supply circuit 12 are buried. A magnetic body 15, which has a function of converging an externally applied magnetic field within the coil 14, is disposed inside the coil 14. A capacitor 16 is connected to the coil 14, thereby forming a resonant circuit. A material with high saturation flux density and high magnetic permeability, such as an amorphous magnetic body or FINEMET(™), is suitable for the magnetic body 15. If a material, which is formed in a thin film, is used as the magnetic body 15, the volume of the magnetic body 15 can advantageously be reduced when the magnetic body 15 is disposed within the capsule endoscope 1. The coil 14 may be an air-core coil which does not have the magnetic body 15.

On the communication unit 6 side, a printed board 17 is disposed at a position spaced apart from and opposed to an inner peripheral surface of the dome-shaped rear end portion 2b2. An RF transmission circuit 18 is disposed on the back surface of the printed board 17. The RF transmission circuit 18 modulates, for example, image information, which is acquired by the CCD 10 and is output from the image processing circuit 11, into an RF signal, and transmits the RF signal.

An antenna 19, which is connected to the transmission circuit 18 and radiates radio waves of the RF signal, and an optical switch 20 are disposed on the front surface of the printed board 17. The antenna 19 is disposed at a substantially central position of the printed board 17.

The optical switch 20 has sensitivity to, e.g. infrared. At least a part of the dome-shaped rear end portion 2b2 of the body cover 2b of the sealed container 2, which is near the optical switch 20, is formed of such a material as to pass infrared at a wavelength to which the optical switch 20 has sensitivity. If infrared is radiated from an infrared emission device (not shown) to the optical switch 20, power supply to the image processing circuit 11 of the capsule endoscope 1 is started from the battery 4 via the power supply circuit 12. The circuit of the optical switch 20 is configured to perform a toggle operation. The capsule endoscope 1 is configured to be kept in the ON state if infrared is once radiated. Besides, such a structure may additionally be provided that when infrared is radiated once again in the ON state, the capsule endoscope 1 is turned off.

When power is supplied to the capsule endoscope 1, the light-emitting element 9 and CCD 10 are driven. An image of a living body tissue in the body cavity, which is illuminated by the light-emitting element 9, is focused on the CCD 10 through the transparent dome of the front end cover 2a and the lens 8, and is thus acquired. The acquired image is properly processed by the image processing circuit 11, sent to the transmission circuit 18, and transmitted from the antenna 19.

A discoid (coin-shaped or cylindrical) magnet 21, which is used for magnetic guidance, is disposed at a part interposed between the battery 4 and the transmission circuit 18. This magnet 21 is magnetized in the radial direction of the capsule endoscope 1. The magnet 21 is disposed such that its magnetic poles are positioned in a direction perpendicular to the major axis direction of the capsule endoscope 1. The angle between the direction of magnetization of the magnet 21 and the direction of the antenna 19 that is connected to the transmission circuit 18 is 90°. This establishes the condition that the magnetic field, which is generated from the magnet 21, is incident at the position of the antenna 19 with a displacement of 90° relative to the direction of the antenna 19. Thereby, the influence on the antenna 19 by the magnetic field from the magnet 21 can be suppressed to a low level. Even if the direction of the antenna 19 and the direction of magnetization of the magnet 21 are positioned with a slight displacement from 90°, the effect of suppressing the influence of the magnetic field on the antenna 19 hardly varies.

A shield member 22 is inserted between the magnet 21 and the transmission circuit 18. The shield member 22 is formed of a magnetic material and has the effect of attracting the magnetic field in the vicinity of the antenna 19. Thereby, the strength of the magnetic field, which is incident on the antenna 19, can be reduced. As a result, the influence of the magnetic field on the structural elements (transmission circuit 18, antenna 19) for wireless communication can be suppressed to a low level, and stable wireless communication can be realized. In the meantime, the battery 4 is held by a heat-shrinkable tube 23. The shield 22 may be dispensed with, if the influence of the magnetic field on the antenna 19 can already be suppressed to a low level (if the strength of transmission from the antenna 19 can be secured), for example, by setting the angle between the direction of the magnetic poles of the magnet 21 and the direction of the antenna 19 at about 90°, thereby to suppress the influence of the magnetic field from the magnet 12 on the antenna 19 to a low level.

Figure 2:
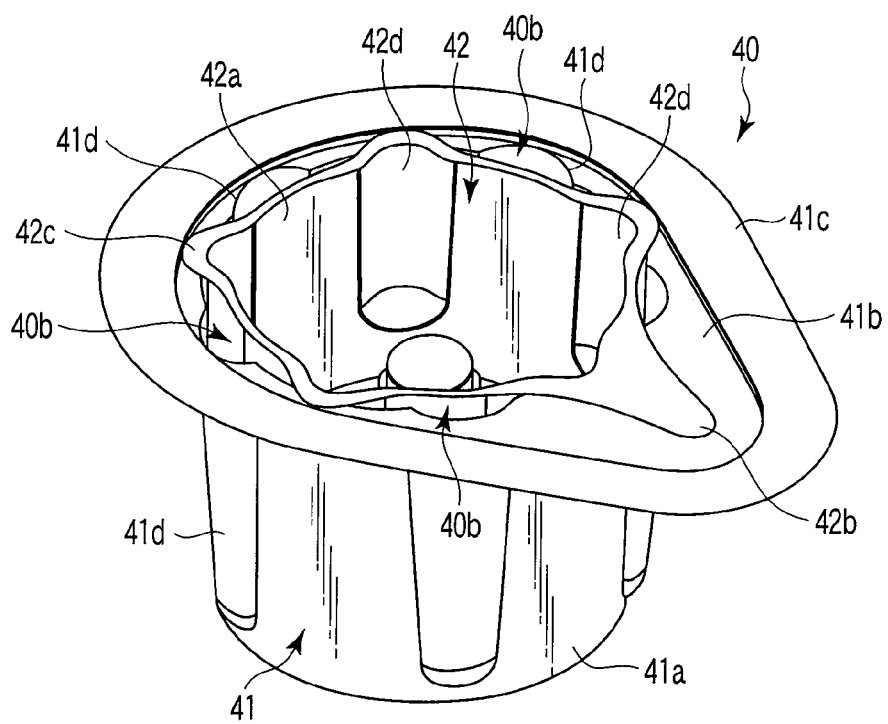
FIG. 2 is a perspective view showing the state in which a sterile sheet is removed from the container case of the capsule endoscope according to the first embodiment.

The capsule medical apparatus container case 40 according to the present embodiment is used in order to keep the sterile state of the capsule endoscope 1 which is sterilized prior to use. As is shown in FIG. 1, the container case 40 includes an outer case 41 which is a blister pack that is formed of an outer container section which is capable of containing the capsule endoscope 1; an inner case 42 which is an inner lid section; and a sterile sheet 43. The inner case 42, as shown in FIG. 2, is provided in the outer case 41 and serves as an inner container section for holding the capsule endoscope 1 between the inner case 42 and the outer case 41. The sterile sheet 43 is provided on upper surfaces of the inner case 42 and outer case 41, and closes the opening of the outer case 41.

Figure 3:
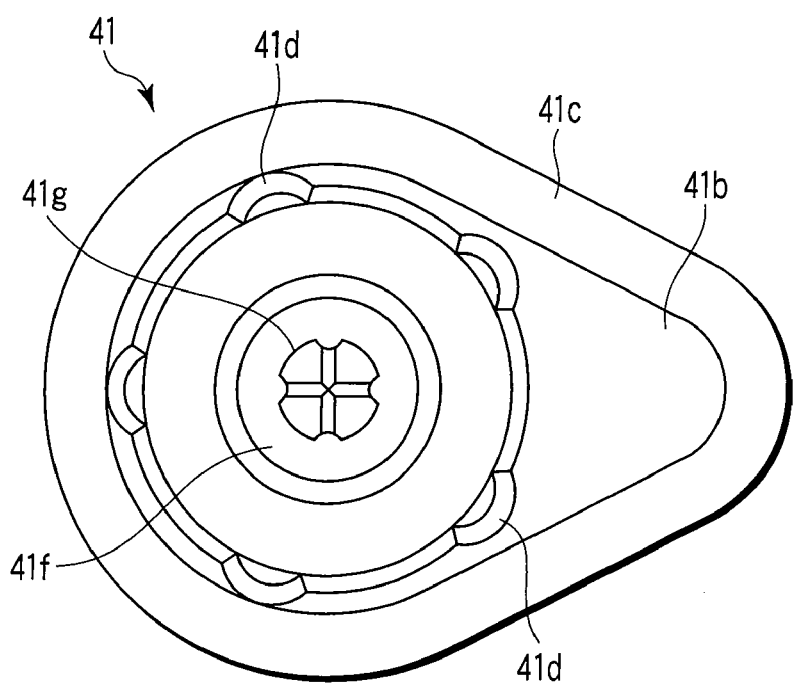
FIG. 3 is a plan view showing an outer case of the container case of the capsule endoscope according to the first embodiment.
Figure 4:
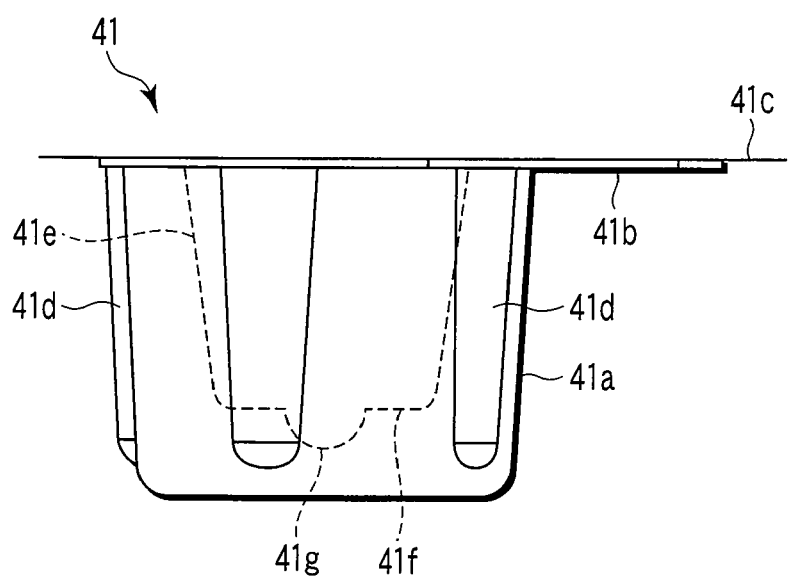
FIG. 4 is a side view showing the outer case of the container case of the capsule endoscope according to the first embodiment.
Figure 7:
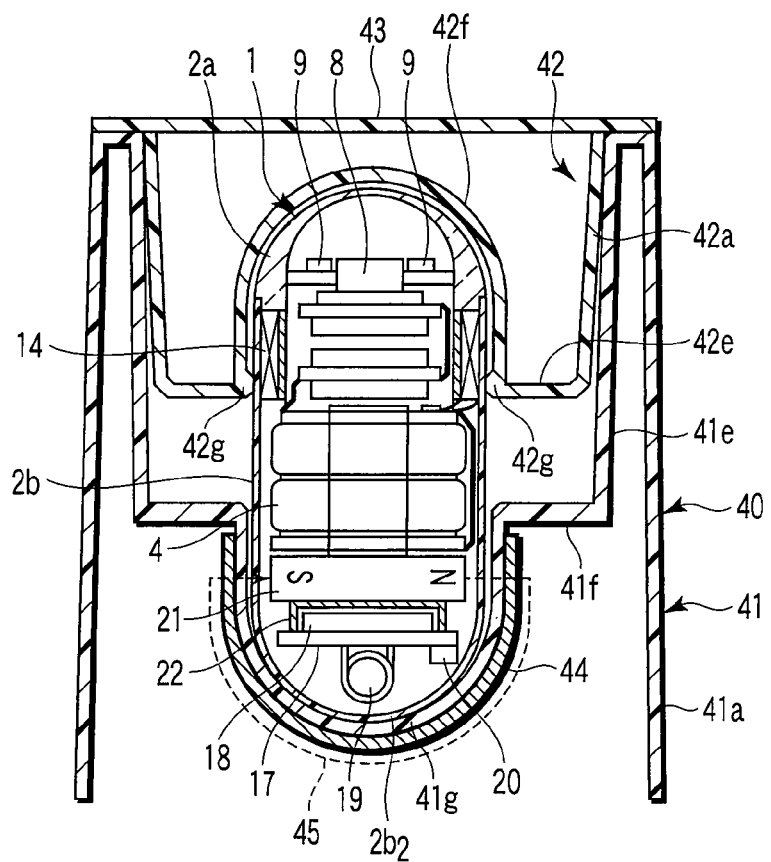
FIG. 7 is a longitudinal cross-sectional view showing the state in which the capsule endoscope is contained in the container case of the capsule endoscope according to the first embodiment.

FIG. 3 is a top view of the container case 40 shown in FIG. 2. FIG. 4 is a side view of the container case 40. FIG. 7 shows a cross-sectional structure of the container case 40. As shown in FIG. 3 and FIG. 4, the outer case 41 includes a circular cylindrical portion 41a and a tongue-shaped tab portion 41b which is provided on a part of an upper opening edge of the circular cylindrical portion 41a. An edge portion 41c is provided on the upper opening edge of the circular cylindrical portion 41a and the outer periphery of the tab portion 41b. In addition, a plurality of projection portions 41d each having a substantially semi-circular columnar shape, which are projected from the inside toward the outside of the circular columnar portion 41a, are provided on the peripheral surface of the circular cylindrical portion 41a.

The projection portion 41d is formed of a projection having a substantially semi-circular columnar shape, which is provided in a longitudinal direction of the circular cylindrical portion 41a. The projection portion 41d has a diameter which is greatest at an upper end (the opening side of the circular cylindrical portion 41a) and gradually decreases toward a lower end (bottom surface 41e side). The projection portions 41d are disposed in the longitudinal direction of the circular cylindrical portion 41a at substantially equal intervals.

As shown in FIG. 7, the outer case 41 of the container case 40 includes a capsule endoscope support base 41e having a bottomed circular cylindrical shape, which is formed to be recessed inward from the upper opening edge portion of the circular cylindrical portion 41a. At a lower end portion of the capsule endoscope support base 41e, an inner bottom portion 41f, which is bent in parallel to the upper edge portion and is formed in a disc shape, is formed. Further, a first hold portion (positioning means) 41g having a recess shape, which holds a part of the capsule endoscope 1, is formed at a central part of the inner bottom portion 41f. The first hold portion 41g is formed in a substantially hemispherical shape. The dome-shaped rear end portion 2b2, which constitutes the body cover 2b of the capsule endoscope 1, is inserted and held in the first hold portion 41g.

Figure 5:
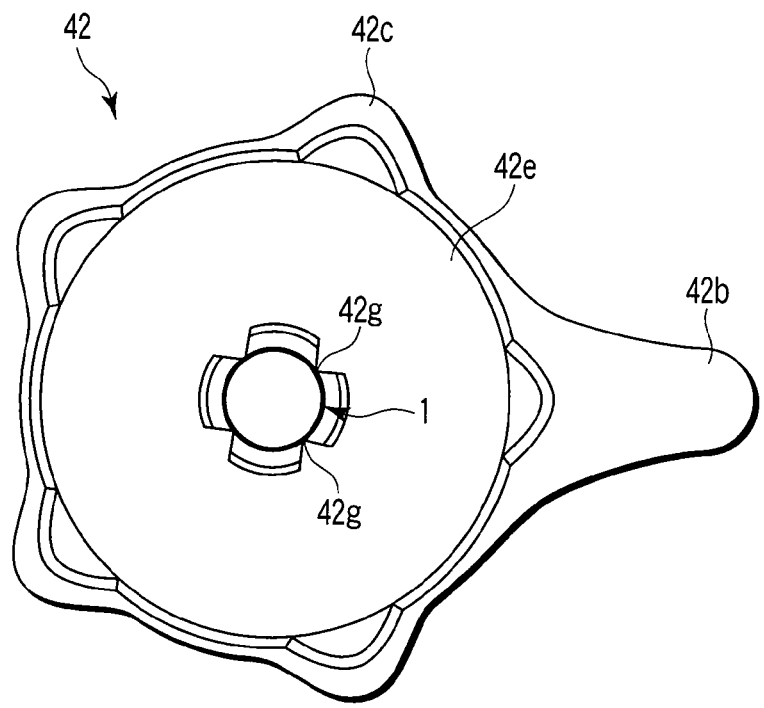
FIG. 5 is a plan view showing an inner case of the container case of the capsule endoscope according to the first embodiment.
Figure 6:
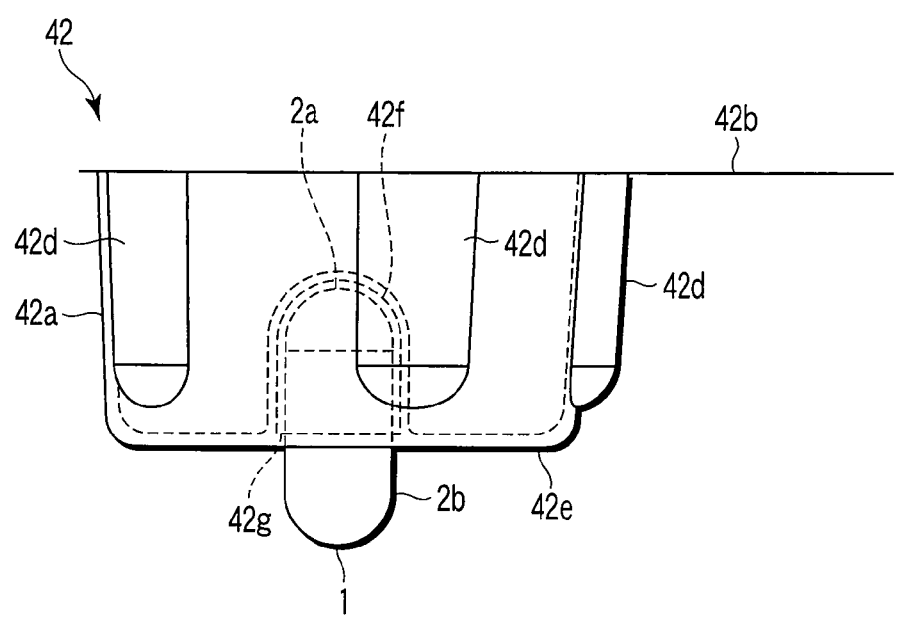
FIG. 6 is a side view showing the inner case of the container case of the capsule endoscope according to the first embodiment.

FIG. 5 and FIG. 6 show the inner case 42. The inner case 42 includes a bottomed circular cylindrical portion 42a and a tongue-shaped tab portion 42b which is provided on a part of an upper opening edge of the circular cylindrical portion 42a. An edge portion 42c, which is continuous with the tab portion 42b, is provided on the upper opening edge of the circular cylindrical portion 42a. In addition, a plurality of projection portions 42d each having a substantially semi-circular columnar shape, which are projected from the inside toward the outside of the circular cylindrical portion 42a, are provided on the peripheral surface of the circular cylindrical portion 42a.

As shown in FIG. 7, the circular cylindrical portion 42a has a bottom surface 42e. A second hold portion (positioning means) 42f, which has an upwardly recessed shape for holding the capsule endoscope 1, is formed at a central part of the bottom surface 42e. The second hold portion 42f is formed in a substantially hemispherical shape. The second hold portion 42f is configured to have an inside diameter that is slightly greater than the outside diameter of the capsule endoscope 1. A plurality of engaging claws 42g, four engaging claws 42g in this embodiment, which project inward, are formed on an inner peripheral surface of a lower end part of the second hold portion 42f. When the dome-shaped front end cover 2a of the capsule endoscope 1 is inserted in the second hold portion 42f, the dome-shaped front end cover 2a is supported and held by the four engaging claws 42g.

The tab portion 42b of the inner case 42 is formed of a substantially triangular plate-shaped member whose upper surface is smaller in size than the tab portion 41b of the outer case 41, thereby to enable easy holding. The tab portion 42b is formed integral with the edge portion 42c provided at the upper opening edge of the circular cylindrical portion 42a. The tab portion 42b is configured to be contactable with the tab portion 41b of the outer case 41 when the inner case 42 is accommodated in the outer casing 41.

The edge portion 42c is provided on the upper opening edge of the circular cylindrical portion 42a and is configured to be contactable with the upper opening edge of the outer case 41 when the inner case 42 is accommodated in the outer case 41. In addition, the thickness of the tab portion 42b and edge portion 42c is set to be less than the thickness of the edge portion 41c of the outer case 41. When the inner case 42 is accommodated in the outer case 41, if the sterile sheet 43 is attached to the edge portion 41c, the entirety of the inner case 42 including the tab portion 42b and edge portion 42c is contained in the outer case 41.

The projection portion 42d is formed of a projection having a substantially semi-circular columnar shape, which is provided in a longitudinal direction of the circular cylindrical portion 42a. The projection portions 42d are disposed in the longitudinal direction of the circular cylindrical portion 42a at substantially equal intervals. The projection portion 42d has an opened upper end and a semi-dome-shaped bottom surface formed at a lower end thereof. In this embodiment, five projection portions 42d are disposed on the peripheral surface of the circular cylindrical portion 42a at substantially equal intervals. The projection portions 42d are configured such that in the state in which the inner case 42 is accommodated in the outer case 41 and the tab portions 41b and 42b are put in contact, most projecting parts of the projection portions 42d can be put in contact with the inner peripheral surface of the circular cylindrical portion 41a at positions not opposed to the projection portions 41d of the outer case 41, thereby preventing looseness of the inner case 42 in the outer case 41.

In the case where the capsule endoscope 1 is contained in the container case 40, as shown in FIG. 7, the capsule endoscope 1 is contained in the state in which the front end cover 2a of the capsule endoscope 1 is positioned upward. At this time, the dome-shaped rear end portion 2b2 of the body cover 2b of the capsule endoscope 1 is inserted and held in the first hold portion 41g of the outer case 41, and the dome-shaped front end cover 2a of the capsule endoscope 1 is inserted and held in the second hold portion 42f of the inner case 42.

Further, in the present embodiment, a magnetic body 44, which forms magnetic force reduction preventing means for the magnet 21 of the capsule endoscope 1, is adhered to the outer peripheral surface of the first hold portion 41g of the outer case 41. The magnetic body 44 is composed of a U-shaped member which is formed in a U shape. The respective end portions of the U-shaped member of the magnetic body 44 are disposed near the respective magnetic poles of the magnet 21 of the capsule endoscope 1 that is contained in the container case 40. In the state in which the capsule endoscope 1 is contained in the container case 40, the U-shaped member of the magnetic body 44 is disposed at a position that is away from the magnet 21 and corresponds to the magnet 21 of the capsule endoscope 1 which is positioned and contained in the container case 40. The magnet 21 and the magnetic body 44 constitute a magnetic circuit 45 so as to connect the N pole and S pole of the magnet 21, as indicated by a broken line in FIG. 7. Thereby, the magnetic field, which leaks from the magnet 21 to the outside of the container case 40, can greatly be decreased, and the reduction in magnetic force of the magnet 21 can be prevented.

With the above-described structure, the following advantageous effects can be obtained. Specifically, in the container case 40 of the magnetic guidance type capsule endoscope 1 according to the present embodiment, the magnetic body 44, which forms magnetic force reduction preventing means for the magnet 21 of the capsule endoscope 1, is adhered to the outer peripheral surface of the first hold portion 41g of the outer case 41. When the capsule endoscope 1, which includes the magnet 21, is set in the container case 40 of the capsule endoscope 1, the capsule endoscope 1 is positioned in the set position in the state in which the dome-shaped rear end portion 2b2 of the body cover 2b of the capsule endoscope 1 is inserted and held in the first hold portion 41g of the outer case 41 and the dome-shaped front end cover 2a of the capsule endoscope 1 is inserted and held in the second hold portion 42f of the inner case 42. Thereby, the U-shaped member of the magnetic body 44 can be disposed at a position that is away from the magnet 21 and corresponds to the magnet 21 of the capsule endoscope 1 which is positioned and contained in the container case 40, and the magnetic circuit 45 can be formed between the U-shaped member of the magnetic body 44 and the respective magnetic poles of the magnet 21. Thereby, the magnetic field, which is generated from the magnet 21 of the capsule endoscope 1, is guided from one of the magnetic poles of the magnet 21 of the capsule endoscope 1 to the other magnetic pole via the U-shaped member of the magnetic body 44 in the container case 40, and the amount of the magnetic field of the magnet 21, which leaks out of the container case 40, can greatly be decreased. As a result, the reduction in magnetic force of the magnet 21 of the capsule endoscope 1, which is contained in the container case 40, can be prevented, and a package of the capsule endoscope 1 with good keeping can be provided. In addition, even in the case where the capsule endoscope 1 is kept in the container case 40 for a long time, the reduction in magnetic force of the magnet 21 can be prevented.

In the container case 40 of the magnetic guidance type capsule endoscope 1 of the present embodiment, since the amount of the magnetic field of the magnet 21 of the capsule endoscope 1, which leaks out of the container case 40, can greatly be decreased, a metallic object on the outside of the container case 40 can be prevented from being attracted to the container case 40 side.

Unlike the prior art, even in the case where a plurality of magnetic guidance type capsule endoscopes 1, which are contained in the container cases 40 of the present embodiment, are stored side by side, it is possible to prevent strong attractive force from acting between the capsule endoscopes 1 due to the magnetic fields of magnets 21 leaking out of the container cases 40, and the efficiency in storage can be improved.

The magnetic body 44 of the above-described U-shaped member may have such a cap shape as to cover the hemispherical first hold portion 41g of the outer case 41. In this case, infrared can be radiated through the outer case 41, thereby to operate the optical switch 20 of the capsule endoscope 1. Thus, in the example of the magnetic body 44 of the U-shaped member, since the optical switch 20 of the capsule endoscope 1 can be operated in the state in which the capsule endoscope 1 is contained in the container case 40, the operability is advantageously excellent.

In the present embodiment, the magnetic body 44 is adhered to the outer peripheral surface of the first hold portion 41g of the outer case 41, but the adhesion may be omitted. Even if the magnetic body 44 is not adhered, the magnetic body 44 rests at a position where the amount of leak of magnetic field to the outside decreases due to the attractive force acting between the magnetic body 44 and the magnet 21 (the magnetic body 44 is attached to the outer case 41 by the magnetic attractive force). In this case, the first hold portion and second hold portion are used in order to fix the capsule endoscope. In other words, the first hold portion and the second hold portion function as fixing means. With this structure, the precision at the time of containing the capsule endoscope 1 in the outer case 41 and inner case 42 may be lowered, and the work of containing can be made easier. Moreover, the work for adhering the magnetic body 44 can be omitted. Besides, the same advantageous effect of suppressing the amount of leak of magnetic field to the outside can be obtained.

Figure 9:
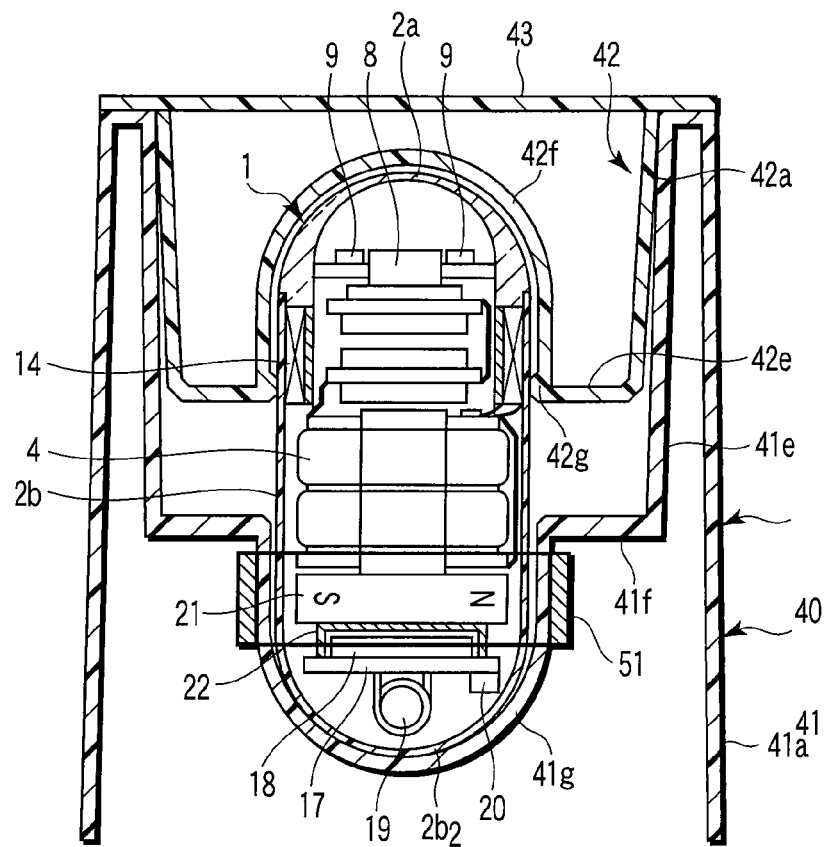
FIG. 9 is a longitudinal cross-sectional view showing the state in which a capsule endoscope is contained in a container case of the capsule endoscope according to a second embodiment of the present invention.
Figure 10:
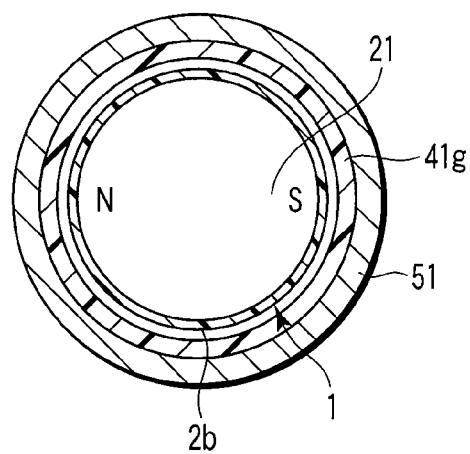
FIG. 10 is a transverse cross-sectional view showing the state of attachment of a magnetic body which is attached to the container case of the capsule endoscope according to the second embodiment.

FIG. 9 and FIG. 10 show a second embodiment of the present invention. In the present embodiment, the structure of the magnetic body 44 of the outer case 41 according to the first embodiment (see FIG. 1 to FIG. 8) is altered as follows.

Specifically, in the present embodiment, as shown in FIG. 9 and FIG. 10, the magnetic body 44 of the U-shaped member of the outer case 41 is replaced with a circular cylindrical magnetic body 51 which is configured to be covered on the hemispherical first hold portion 41g of the outer case 41. In this case, the circular cylindrical magnetic body 51 is configured to have a length of the circular cylinder, which is greater than the length of the magnet 21 in the direction of the magnetic poles, relative to the magnet 21 of the capsule endoscope 1. In the present embodiment, too, the same advantageous effects as in the first embodiment can be obtained.

FIG. 11 shows a modification of the magnetic body 51 which is attached to the container case 40 of the capsule endoscope 1 according to the second embodiment. In the present modification, the circular cylindrical magnetic body 51 is replaced with a substantially U-shaped magnetic body 52, as shown in FIG. 11, which is configured to be covered on the hemispherical first hold portion 41g of the outer case 41.

In the present modification, the U-shaped member of the magnetic body 52 is disposed at a position that is away from the magnet 21 and corresponds to the magnet 21 of the capsule endoscope 1 which is positioned at the set position of the container case 40 and contained in the container case 40, and the magnetic circuit 45 can be formed between the U-shaped member of the magnetic body 52 and the respective magnetic poles of the magnet 21. Therefore, with this modification, too, the same advantageous effects as in the first embodiment can be obtained.

FIG. 12 to FIG. 14 show a third embodiment of the present invention. In the present embodiment, the capsule endoscope 1 of the first embodiment (see FIG. 1 to FIG. 8) is replaced with a capsule endoscope 61 having a different structure, and a container case 62 for this capsule endoscope 61 is provided. The other structural parts are the same as those in the first embodiment, and the same parts as in the first embodiment are denoted by like reference numerals and a description is omitted.

Specifically, in the capsule endoscope 61 of the present embodiment, a circular cylindrical magnet 35, as shown in FIG. 14, is provided as the magnet that is used for magnetic guidance of the capsule endoscope 61. The magnet 35 is mounted on the outer peripheral surface of the mold member 13 in which the image processing circuit 11 and power supply circuit 12 of the capsule endoscope 61 are molded. As shown in FIG. 13, the magnet 35 is disposed such that their magnetic poles are arranged in the major axis direction of the capsule endoscope 61.

Further, in the capsule endoscope 61 of the present embodiment, two coils 31 and 32 are substituted for the coil 14 for detecting the position of the capsule endoscope 1 of the first embodiment. These two coils 31 and 32 are disposed in a part between the battery 4 and the transmission circuit 18. The two coils 31 and 32 are disposed substantially perpendicular to each other. The two coils 31 and 32 do not necessarily intersect at 90°, and may interest at a proper angle. Capacitors 32 and 33 are connected to the two coils 31 and 32, thereby forming resonant circuits, respectively.

In the container case 62 of the present embodiment, as shown in FIG. 14, a circular cylindrical magnetic body 63 is disposed on the outer periphery of the second hold portion 42f of the inner case 42. The magnetic body 63, as shown in FIG. 12, is configured to have a length of the circular cylinder, which is greater than the length of the magnet 61 in the direction of the magnetic poles, relative to the magnet 61 of the capsule endoscope 61.

The following advantageous effects can be obtained by the above-described structure. Specifically, in the present embodiment, the circular cylindrical magnetic body 63 is disposed on the outside of the inner case 42 of the container case 62 which is a package of the capsule endoscope 61. The capsule endoscope 61 is contained inside the inner case 42 of the container case 62. The circular cylindrical magnetic body 63 is disposed on the outer peripheral surface of the second hold portion 42f of the inner case 42 of the container case 62. With this structure, the magnetic body 63 and the magnet 35 constitute a magnetic circuit so as to connect the N pole and S pole of the magnet 35, and the amount of the magnetic field of the magnet 35, which leaks to the outside, can greatly be decreased, and the reduction in magnetic force of the magnet 35 can be prevented. Thereby, the reduction in package of the container case 62 of the capsule endoscope 61 and the improvement in portability can be achieved.

A double coated adhesive tape, for instance, is attached to the magnetic body 63, and the magnetic body 63 may be configured to be adhered to the capsule endoscope 61. In this case, the magnetic body 63 is detached before the capsule endoscope 61 is used.

Without attaching the double coated adhesive tape (adhesive member) to the magnetic body 63, the magnetic body 63 may be attached to the capsule medical apparatus 61 by making use of attractive force acting between the magnetic body 35 and the magnetic body 63. In this case, too, the magnetic body 63 is detached before the capsule endoscope 61 is used. A resin material may be coated on the magnetic body 63. Besides, the magnetic body 63 may be configured to be sandwiched (laminated) between or covered with resin films (resin material).

Figure 15:
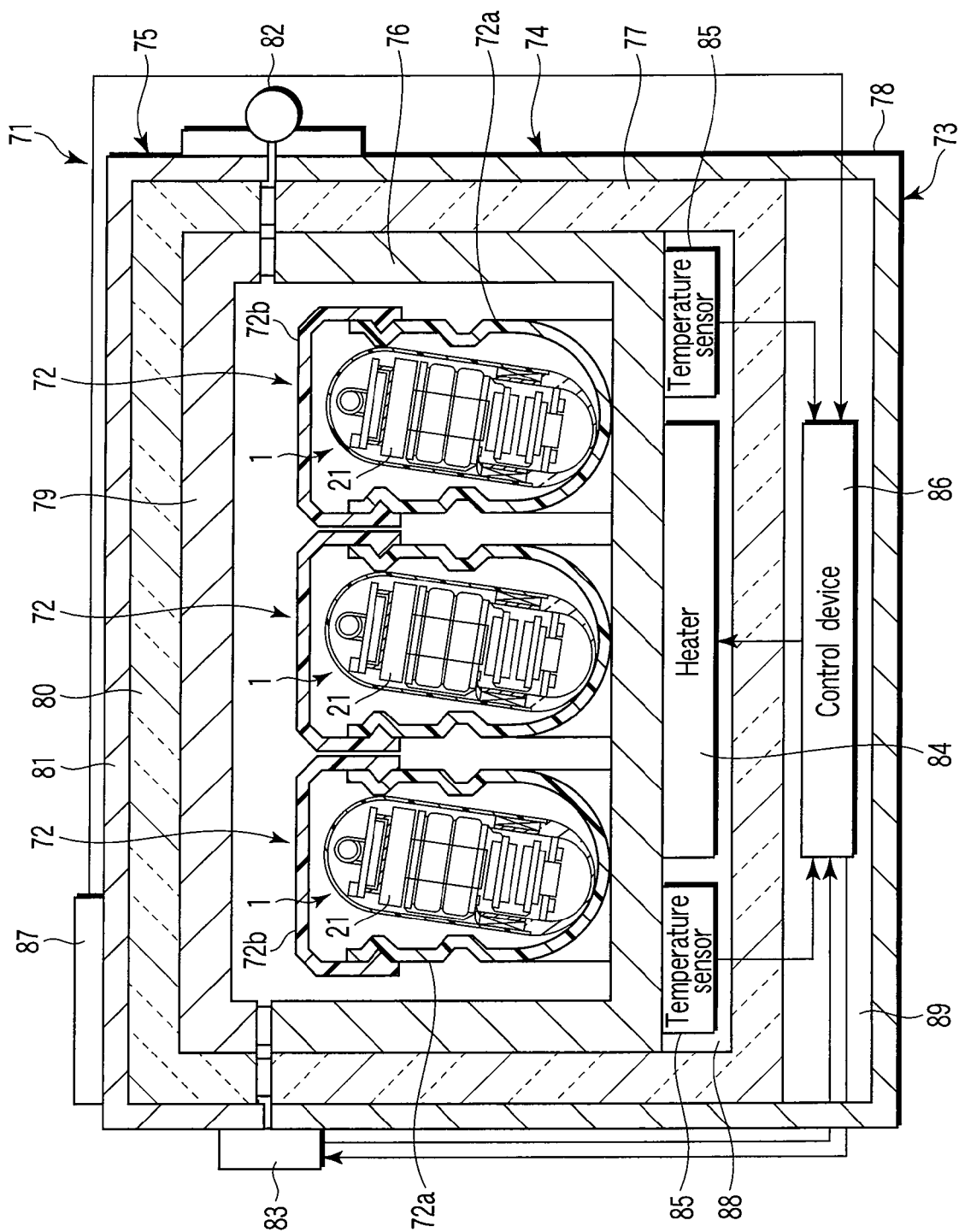
FIG. 15 is a longitudinal cross-sectional view that schematically shows the structure of a discarding device of capsule endoscopes for magnetic guidance.

FIG. 15 shows a discarding device 71 which demagnetizes the magnet 21 for magnetic guidance of the capsule endoscope 1, and discards the capsule endoscope 1. A plurality of discarding cases 72, three discarding cases 72 in this example, are accommodated in the discarding device 71.

The discarding case 72 includes a bottomed circular cylindrical case body 72a which contains the capsule endoscope 1 that has been used, and a cover body 72b which closes an upper opening portion of the case body 72a. The capsule endoscope 1, which is taken out of the body cavity, is contained the discarding case 72 in the state in which the capsule endoscope 1 is not cleaned.

The discarding device 71 is provided with a heat insulation container 73. The heat insulation container 73 includes a container body 74 having an opening in its upper surface, and a cover body 75 which closes the upper opening portion of the container body 74. The container body 74 has a three-layer structure comprising a stainless container 76 that is an inner container, a heat insulation layer 77, and an armor member 78 that is an outer container. Similarly, the cover body 75 has a three-layer structure comprising a stainless cover 79 that is an inner cover, a heat insulation layer 80, and an armor member 81 that is an outer cover.

One end portion of the cover body 75 is rotatably coupled to one end portion of the heat insulation container 73 via a hinge portion 82. Thereby, the upper opening portion of the heat insulation container 73 can be closed and opened by the rotating operation of the cover body 75 about the hinge portion 82. The other end portion of the cover body 75 is disengageably engaged with the other end portion of the heat insulation container 73 via a lock device 83. The cover body 75 is fixed to the heat insulation container 73 by the lock device 83 in the state in which the cover body 75 is moved to the position where the cover body 75 airtightly closes the upper opening portion of the heat insulation container 73.

A first isolation chamber 88, which is isolated from the inside of the heat insulation container 73, is formed between the stainless container 76 of the heat insulation container 73 and the heat insulation layer 77. In addition, a second isolation chamber 89, which is isolated, is formed between the heat insulation layer 77 and the armor member 78. A heater 84, which is fixed to a bottom surface of the stainless container 76, and a plurality of temperature sensors 85 are provided in the first isolation chamber 88.

A control device 86 of the discarding device 71 is provided in the second isolation chamber 89. The heater 84 and plural temperature sensors 85 are connected to the control device 86. A switch 87 of the discarding device 71 is attached to the surface of the cover body 75. The switch 87 is connected to the control device 86.

Next, the operation of the discarding device 71 having the above-described structure is described. The heat insulation chamber 73 of the discarding device 71 with the above-described structure has such a size as to be able to accommodate a plurality of discarding cases 72 at a time, and a discarding process for a plurality of capsule endoscopes 1 can be performed at a time.

When the discarding device 71 is used, plural discarding cases 72 are contained in the heat insulation container 73. In the state in which the discarding cases 72 storing the capsule endoscopes 1 are contained in the discarding device 71, the cover body 75 is closed. In the state in which the cover body 75 is fixed to the heat insulation container 73, the cover body 75 is locked by the lock device 83.

Figure 16:
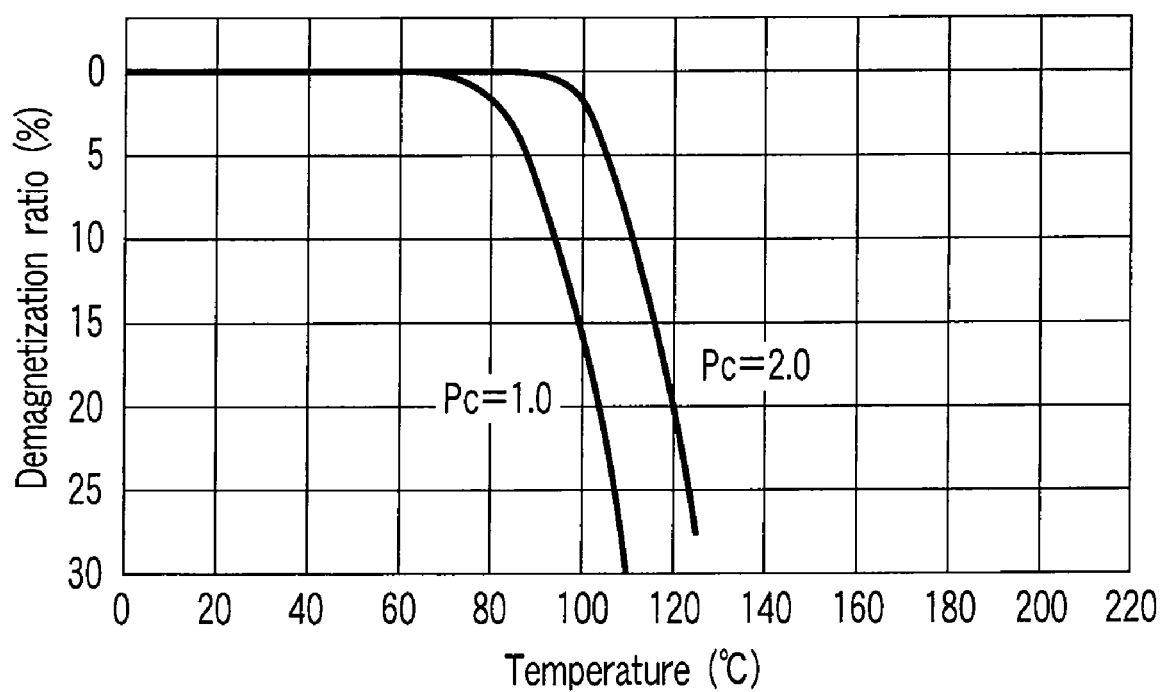
FIG. 16 is a characteristic diagram showing the relationship between a heating temperature of the magnet and a demagnetization ratio.

In this state, when the switch 87 is operated, the control device 86 operates the heater 84 and heats the inside of the stainless container 76. The temperature of the stainless container 76 is monitored by the temperature sensors 85, and a temperature control is executed by the control device 86. For example, the temperature in the heat insulation container 73 is controlled at, e.g. 150° C. At this time, demagnetization of the magnet 21 in the capsule endoscope 1 begins at about 100° C., as shown in a temperature characteristic graph of FIG. 16, and the magnet 21 is substantially demagnetized at about 150° C.

After the temperature in the stainless container 76 is kept at high temperatures for a predetermined time, the control device 86 stops heating by the heater 84. In this state, the control device 86 controls the lock device 83 so that the lock device 83 of the cover body 75 may not be opened by an operation from outside.

Thereafter, the temperature in the stainless container 76 is monitored by the temperature sensors 85. After confirming the state in which the temperature has lowered to, e.g. about 40° C., the control device 86 unlocks the lock device 83 of the cover body 75. Thereby, the cover is set in the state in which the cover can be opened by the operator. In this state, the operator opens the cover body 75, takes out the capsule endoscopes 1 from the stainless container 76 and discards them.

The following advantageous effects can be obtained by the discarding device 71 with the above-described structure. Specifically, the used capsule endoscopes 1 are contained in the discarding cases 72, and stored in the discarding device 71. In this state, a heating process is executed to keep the temperature in the stainless container 76 at high temperatures of about 150° C. Thereby, in the state in which the magnetic force of the magnet 21 of the capsule endoscope 1 is eliminated or greatly decreased, the capsule endoscope 1 can be discarded. This prevents the phenomenon that a metallic object is attracted by the magnetic force of the magnet 21 of the capsule endoscope 1 for magnetic guidance, resulting in difficulty in discarding. Therefore, the efficiency in discarding of the capsule endoscope 1 is enhanced.

In the present embodiment, the heating temperature is set at about 150° C., but the heating temperature may be set on the basis of the temperature characteristics of the magnet 21 or the temperature characteristics of the armor or structural part of the capsule endoscope 1. To be more specific, a material having a Curie temperature, which is lower than the heat resistance temperature of the armor or structural part of the capsule endoscope 1, is used as the material of the magnet 21. The heat resistance temperature of the armor or structural part of the capsule endoscope 1 is, for example, a temperature at which the resin material of the armor is not softened. The heating by the discarding device is performed as a work for discarding the magnet 21 provided in the capsule endoscope 1 that is so designed as to meet this condition. The heating temperature at this time is set to be higher than the Curie temperature of the magnet 21 and to be lower than the heat resistance temperature of the armor or structural part of the capsule endoscope 1. Thereby, the magnet 21 can be demagnetized and the state in which the shape of the capsule endoscope 1 is unchanged can be maintained. This makes the discarding easier. The discarding container shown in this embodiment is usable for the medical apparatus containing devices shown in the preceding embodiments.

The description of the embodiments of the present invention has been directed to the use of the capsule endoscopes. However, the embodiments are applicable to, for instance, endoscopes apparatuses incorporating magnets or catheters incorporating magnets. If a magnetic body is disposed in the vicinity of a part of an endoscope apparatus case, where that portion of an endoscope insertion section, which incorporates a magnet, is stored, it becomes possible to suppress radiation of magnetic field from the magnet to the space to a low level even in the endoscope apparatus incorporating the magnet, and the same advantageous effects can be obtained.

Alternatively, a magnetic body may be adhered to an outer surface in the vicinity of that portion of the insertion section of the endoscope apparatus, which incorporates the magnet. In this case, the magnetic body is removed from the endoscope apparatus at a time of use. In this case, too, the same advantageous effects can be obtained, that is, the radiation of magnetic field from the magnet to the space can be suppressed to a low level, and the reduction in magnetic force of the magnet can be suppressed.

In the case of a catheter incorporating a magnet, the magnetic body may be configured to be disposed in the vicinity of a part of a container device that contains the catheter, where that part of an insertion section of the catheter, which is inserted in the body and which includes the magnet, is stored. In this case, too, the same advantageous effects can be obtained, that is, the radiation of magnetic field from the magnet to the space can be suppressed to a low level, and the reduction in magnetic force of the magnet can be suppressed.

Alternatively, the magnetic body may be configured to be adhered to the vicinity of that part of the insertion section of the catheter, which is inserted in the body and in which the magnet is disposed. In this case, too, the same advantageous effects can be obtained, that is, the radiation of magnetic field from the magnet to the space can be suppressed to a low level, and the reduction in magnetic force of the magnet can be suppressed.

Furthermore, the invention is applicable to a container device for an instrument which is attached to a distal end of an endoscope and which incorporates a magnet. In this case, the container device may be configured to contain, in place of the capsule endoscope 1 of the first to third embodiment, the instrument which is attached to the distal end of the endoscope and which incorporates the magnet. In this case, too, the same advantageous effects can be obtained, that is, the radiation of magnetic field from the magnet to the space can be suppressed to a low level, and the reduction in magnetic force of the magnet can be suppressed.

The invention is also applicable to a container device for an instrument which is stayed in a body cavity, for example, a tissue of the stomach or intestine, and which is composed of a magnet or incorporates a magnet. This instrument, after stayed, can pull the tissue, where the instrument is stayed, by a magnetic field from outside of the body, and endoscopic treatment can be performed in the state in which the tissue is pulled. In this case, the container device may be configured to contain, in place of the capsule endoscope 1 of the first to third embodiment, the instrument which is attached to the distal end of the endoscope and which incorporates the magnet. In this case, too, the same advantageous effects can be obtained, that is, the radiation of magnetic field from the magnet to the space can be suppressed to a low level, and the reduction in magnetic force of the magnet can be suppressed.

As regards the discarding device, the discarding device is applicable not only to the capsule endoscopes, but also to the catheter, the instrument which is attached to the distal end of the endoscope and which incorporates the magnet, or the instrument which is stayed in the body cavity, for example, the tissue of the stomach or intestine, and which is composed of the magnet or incorporates the magnet. In this case, the magnet of the medical apparatus (the catheter, the instrument which is attached to the distal end of the endoscope and which incorporates the magnet, or the instrument which is stayed in the body cavity, for example, the tissue of the stomach or intestine, and which is composed of the magnet or incorporates the magnet) can be demagnetized, and the discarding of the medical apparatus can be made easier.

Not only in the structure wherein a magnet is disposed in a medical apparatus but also in the structure wherein a magnet is attached to a medical apparatus container device, a magnetic body may be disposed in the vicinity of the magnet. Thereby, spreading of the magnetic field, which is generated from the magnet, can advantageously be suppressed. Specifically, this structure is applicable to a medical apparatus container section for a medical apparatus, the operation mode of which varies between the state in which the magnet is present near the medical apparatus and the state in which the magnet is not present near the medical apparatus. In this case, the magnetic body may be provided on that side of the magnet, which is opposite to the medical apparatus. The magnetic force, which is generated from the magnet, is radiated to the capsule side, and the operation mode of the capsule can be maintained in the state in which the magnet is present near the capsule. In this state, since the magnetic body is present on that side of the magnet, which is opposite to the medical apparatus, the magnetic force from the magnet penetrates the magnetic body and does not easily leak to the outside.

Needless to say, the present invention is not limited to the above-described embodiments, and various modifications may be made without departing from the spirit of the invention.

Other characteristic technical matters of the present invention are described below.

Note (Item 1) A capsule medical apparatus containing device for containing a capsule medical apparatus which incorporates a magnet, comprising positioning means for positioning the capsule medical apparatus, and a magnetic body which is so disposed as to guide a magnetic field, which is generated from the magnet of the capsule medical apparatus that is positioned by the positioning means, from one magnetic pole to the other magnetic pole.

(Item 2) A discarding device comprising a heat insulation container which contains a plurality of discarding cases each accommodating a capsule endoscope including a magnet, and heating means for performing a heating process to vary a temperature in the heat insulation container to a temperature of a state in which a magnetic force of the magnet is eliminated or greatly decreased, wherein the magnet of the capsule endoscope is demagnetized and then discarded.

The present invention is effective in a technical field of a capsule medical apparatus containing device which contains a magnetic guidance type capsule endoscope, and in a technique field of manufacture of the capsule medical apparatus containing device.

What is claimed is:

1. A medical apparatus containing device, comprising:
a container case configured to contain a medical apparatus, wherein the medical apparatus incorporates a magnet including a first magnetic pole and a second magnetic pole for generating a magnetic field;
a positioning mechanism configured to position the medical apparatus in the container case in a predefined orientation, when the medical apparatus is contained in the container case; and
a magnetic body in the container case which is positioned relative to the magnet of the medical apparatus when contained so as to guide the magnetic field between the first magnetic pole and the second magnetic pole through the magnetic body, so as to decrease magnetic field leakage outside of the container case when the medical apparatus is contained in the container case and positioned therein by the positioning mechanism,
wherein the magnetic body is configured to be disposed so as to surround the magnet when the medical apparatus is contained in the container case and positioned by the positioning mechanism; and
wherein the medical apparatus is a capsule medical apparatus,
the container case includes an outer case and an inner case,
the positioning mechanism includes a first hold portion formed on the outer case and having a respective recess shape and a second hold portion formed on the inner case and having a respective recess shape, and the first and the second hold portions are configured to hold a part and another part of the capsule medical apparatus, respectively, when the medical apparatus is contained in the container case, and
the magnetic body is mounted on an outside of at least one of the first hold portion and the second hold portion.

2. The medical apparatus containing device according to claim 1, wherein the magnetic body is formed as a thin film.

3. The medical apparatus containing device according to claim 2, wherein the thin film is coated with a resin material.

4. The medical apparatus containing device according to claim 3, wherein an adhesive member is attached to the resin material, and the resin material is attached to at least one of the medical apparatus and the medical apparatus containing device.

5. The medical apparatus containing device according to claim 1, wherein the magnetic body is configured to be positioned relative to at least one of the medical apparatus and the medical apparatus containing device by an attractive force acting between the magnetic body and the magnet when the medical apparatus is contained in the container case and positioned by the positioning mechanism.

6. The medical apparatus containing device according to claim 1,
wherein the magnetic body is configured to prevent reduction of the magnetic force of the magnet when the medical apparatus is contained in the container case and positioned by the positioning mechanism.

7. The medical apparatus containing device according to claim 1,
wherein the magnetic body has a U-shape, includes a first end portion and a second end portion and is configured to be disposed such that each of the first and second end portions is respectively disposed in a vicinity of the first and second magnetic poles, respectively, when the medical apparatus is contained in the container case and positioned by the positioning mechanism.

* * * * *